United States Patent
McKinnie

(10) Patent No.: US 7,851,662 B2
(45) Date of Patent: *Dec. 14, 2010

(54) PREPARATION AND PROVISION OF HIGH ASSAY DECABROMODIPHENYLETHANE

(75) Inventor: Bonnie Gary McKinnie, Magnolia, AR (US)

(73) Assignee: Albemarle Corporation, Richmond, VA (US)

(*) Notice: Subject to any disclaimer, the term of this patent is extended or adjusted under 35 U.S.C. 154(b) by 595 days.

This patent is subject to a terminal disclaimer.

(21) Appl. No.: 11/840,325

(22) Filed: Aug. 17, 2007

(65) Prior Publication Data

US 2008/0228015 A1    Sep. 18, 2008

Related U.S. Application Data

(60) Provisional application No. 60/895,376, filed on Mar. 16, 2007.

(51) Int. Cl.
*C07C 17/00* (2006.01)
*C07C 22/00* (2006.01)

(52) U.S. Cl. .................. 570/190; 570/182; 570/184; 570/199

(58) Field of Classification Search .......... 570/182, 570/190, 184, 199
See application file for complete search history.

(56) References Cited

U.S. PATENT DOCUMENTS

| | | | |
|---|---|---|---|
| 3,752,856 A | 8/1973 | Nagy et al. |
| 3,965,197 A | 6/1976 | Stepniczka |
| 4,847,428 A | 7/1989 | Gu |
| 5,008,477 A | 4/1991 | Hussain |
| 5,030,778 A | 7/1991 | Ransford |
| 5,077,334 A | 12/1991 | Hussain |
| 5,124,496 A | 6/1992 | Templeton et al. |
| 5,302,768 A | 4/1994 | Hussain |
| 5,324,874 A | 6/1994 | Ransford et al. |
| 5,401,890 A | 3/1995 | Parks |
| 5,457,248 A | 10/1995 | Mack et al. |
| 5,741,949 A | 4/1998 | Mack |
| 6,008,283 A | 12/1999 | Rose et al. |
| 6,518,468 B1 | 2/2003 | Parks et al. |
| 6,603,049 B1 | 8/2003 | Parks et al. |
| 6,768,033 B2 | 7/2004 | Parks et al. |
| 6,841,702 B2 | 1/2005 | Magdolen et al. |
| 6,958,423 B2 | 10/2005 | Parks et al. |
| 6,974,887 B2 | 12/2005 | Parks et al. |
| 7,129,385 B2 | 10/2006 | Dawson et al. |
| 2003/0144563 A1 | 7/2003 | Falloon et al. |
| 2004/0110996 A1 | 6/2004 | Parks et al. |

FOREIGN PATENT DOCUMENTS

| | | |
|---|---|---|
| CA | 2094469 | 9/2005 |
| CN | 1429800 | 7/2003 |
| DE | 2400455 A1 | 2/1975 |
| DE | 2950877 A1 | 6/1981 |
| DE | 3326343 | 1/1985 |
| EP | 0107978 A1 | 5/1984 |
| EP | 0347116 A2 | 12/1989 |
| EP | 0445595 A2 | 9/1991 |
| EP | 0571859 A2 | 12/1993 |
| GB | 981833 | 1/1965 |
| GB | 1411524 | 10/1975 |
| GB | 2143521 | 2/1985 |
| JP | 50018430 | 2/1975 |
| JP | 52039639 | 3/1977 |
| JP | 52139033 | 11/1977 |
| JP | 53053629 | 5/1978 |
| JP | 53116332 | 10/1978 |
| JP | 54044623 | 4/1979 |
| JP | 58222043 | 12/1983 |
| JP | 62004241 | 1/1987 |
| JP | 10158202 | 6/1998 |
| JP | 10175893 | 6/1998 |
| WO | WO 93/24434 A1 | 12/1993 |
| WO | WO 94/22978 A1 | 10/1994 |
| WO | WO 03/055832 A1 | 7/2003 |

OTHER PUBLICATIONS

Yang, Ze-hui, et al., "Technological Progress in Catalytic Synthesis of Decabromodiphenyl Ether by Brominating Diphenyl Oxide with Bromine Chloride", Fine Chemicals, vol. 19, Jan. 2002, pp. 42-44, abstract only translated.
Albemarle Corporation, XP002458574, Saytex 8010 Flame Retardant, Brochure, 2001, 2 pages.

*Primary Examiner*—Jafar Parsa
(74) *Attorney, Agent, or Firm*—Jeremy J. Kliebert

(57) ABSTRACT

High assay reaction-derived decabromodiphenylethane product is produced and provided. The process comprises feeding diphenylethane, a partially brominated diphenylethane, or both subsurface into the liquid phase of a reaction mixture formed from components comprising excess liquid bromine and aluminum-based Lewis acid bromination catalyst. The temperature of the reaction mixture, the catalyst concentration in the excess bromine in the reaction mixture, and the feed time are coordinated in the processes to produce high assay reaction-derived decabromodiphenylethane product. Ways of effecting such coordination are described.

9 Claims, No Drawings

US 7,851,662 B2

PREPARATION AND PROVISION OF HIGH ASSAY DECABROMODIPHENYLETHANE

REFERENCE TO RELATED APPLICATION

This application claims the benefit and priority of U.S. Provisional Application No. 60/895,376, filed Mar. 16, 2007, the disclosure of which is incorporated herein by reference.

TECHNICAL FIELD

This invention relates to the preparation and provision of high assay reaction-derived decabromodiphenylethane products and their use.

BACKGROUND

Decabromodiphenylethane is a time-proven flame retardant for use in many flammable macromolecular materials, e.g. thermoplastics, thermosets, cellulosic materials and back coating applications of very high quality.

Governmental regulating agencies tend to be moving away from partially brominated analogs and more towards perbrominated compounds as evidenced by the recent EU RoHS (Restriction on Hazardous Substances) directive (2002/95/EC) relating in part to partially brominated diphenyl oxides. Even with the exemption of decabromodiphenyl oxide from RoHS per 2005/717/EC, the regulations have not been clear enough in terms of the acceptable nonabromodiphenyl oxide content in electrical and electronic products. Some end users therefore find it uncomfortable using the commercial decabromodiphenyl oxide in which significant amounts of nonabromodiphenyl oxide exists as impurity. In order to meet the strictest interpretation of RoHS by the end users, a high purity version of decabromodiphenyl oxide is being marketed by Albemarle Corporation. In view of the confusion concerning the presence of small quantities of lower brominated impurities in the flame retardant products, there is thus a need in the market place for high assay perbrominated flame retardants.

Decabromodiphenylethane is presently sold as a powder derived from the bromination of 1,2-diphenylethane. Among prior processes for effecting such bromination are the bromination processes described in U.S. Pat. Nos. 6,518,468; 6,958,423; 6,603,049; 6,768,033; and 6,974,887. Decabromodiphenylethane has been commercially produced by the assignee of this application for many years using a standard process. Each batch of product was analyzed by a GC procedure. A review of the GC analyses indicated that the average bromine content of over 4000 batches of decabromodiphenylethane product was 97.57 area percent with a 3-sigma precision of ±1.4 area percent. In some cases, the analysis of the product from a given run provided assays of decabromodiphenylethane in the region of about 99 area percent and above, and in some other cases significantly lower GC assays were obtained. The reasons for this variance cannot be established from the information available.

Gas chromatographic analysis of commercial decabromodiphenylethane products available in the marketplace from other manufacturers have, in some cases, also given assays of a decabromodiphenylethane product as high as about 99.6 area percent. In other cases, GC analyses of commercial decabromodiphenylethane products available in the marketplace have indicated the presence of much lower amounts of decabromodiphenylethane in the product. Information on the method by which such high assay products were produced and the purification procedures used, if any, is not generally available to the public.

From at least the standpoint of providing environmentally-friendly process technology, it would be highly desirable if commercially feasible processes could be found that would produce on a consistent basis a decabromodiphenylethane product that comprises at least about 99.0 GC area percent of decabromodiphenylethane ($Br_{10}DPE$), with the balance consisting essentially of nonabromodiphenylethane ($Br_9DPE$). Such product is hereinafter often referred to in the specification and claims hereof as "high assay decabromodiphenylethane product". Moreover, this high assay decabromodiphenylethane product is a "reaction-derived" product which term as used herein including the claims, means that the composition of the product is reaction determined and not the result of use of downstream purification techniques, such as recrystallization or chromatography, or like procedures that can affect the chemical composition of the product. Adding water or an aqueous base such as sodium hydroxide to the reaction mixture to inactivate the catalyst, and washing away of non-chemically bound impurities by use of aqueous washes such as with water or dilute aqueous bases are not excluded by the term "reaction-derived". In other words, the products are directly produced in the synthesis process without use of any subsequent procedure to remove or that removes nonabromodiphenylethane from decabromodiphenylethane.

BRIEF SUMMARY OF THE INVENTION

As a result of extensive research studies, commercially feasible processes have been discovered that can produce a decabromodiphenylethane product that comprises at least about 99.0 GC area percent of decabromodiphenylethane ($Br_{10}DPE$), with the balance consisting essentially of nonabromodiphenylethane ($Br_9DPE$). The reaction-derived decabromo-diphenylethane products producible by this invention typically contain $Br_{10}DPE$ together with at least a small detectable amount of $Br_9DPE$. However, it is not inconceivable that the process technology of this invention may enable production of reaction-derived $Br_{10}DPE$ having no detectable $Br_9DPE$.

More particularly, pursuant to this invention high assay reaction-derived decabromodiphenylethane product is produced by a process which comprises feeding (i) diphenylethane (DPE), (ii) partially brominated diphenylethane having a bromine number less than about two (pb-DPE), or (iii) both of (i) and (ii) subsurface into the liquid phase of a reaction mixture formed from components comprising excess liquid bromine and aluminum-based Lewis acid bromination catalyst, wherein the temperature of the reaction mixture, the catalyst concentration, and the feed time are coordinated to produce high assay reaction-derived decabromodiphenylethane product. By properly coordinating the temperature of the reaction mixture, the catalyst concentration, and the feed time, high assay reaction-derived decabromodiphenylethane product can be produced on a consistent basis from run to run.

This invention also provides reaction-derived decabromodiphenylethane product produced by a process of this invention, which product comprises at least about 99.0 GC area percent of decabromodiphenylethane ($Br_{10}DPE$), with the balance consisting essentially of nonabromodiphenylethane ($Br_9DPE$). In a preferred embodiment, this invention provides reaction-derived decabromodiphenylethane product produced by a process of this invention, which product comprises at least about 99.5 GC area percent of decabromodiphenylethane ($Br_{10}DPE$), with the balance consisting essentially of nonabromodiphenylethane ($Br_9DPE$). In a more preferred embodiment, this invention provides reaction-derived decabromodiphenylethane product produced by a process of this invention, which product comprises at least about 99.7 GC area percent of decabromodiphenylethane ($Br_{10}DPE$), with the balance consisting essentially of nonabromodiphenylethane ($Br_9DPE$).

The above and other embodiments and features of this invention will be still further apparent from the ensuing description and appended claims.

FURTHER DETAILED EXPLANATION OF UNDERLYING FEATURES OF THIS INVENTION ENABLING PROPER COORDINATION OF REACTION CONDITIONS

As noted above, to achieve the preparation of high assay reaction-derived decabromodiphenylethane product, several reaction variables are coordinated with each other in ways that result in the production of such product in a commercially feasible manner. In order to understand the interrelationship among these reaction variables, the following underlying concepts developed pursuant to this invention on the basis of extensive research studies have been taken into consideration:

First of all, assay of the decabromodiphenylethane product produced by feeding DPE and/or pb-DPE to a reaction mixture containing a large excess of liquid bromine and an aluminum-based catalyst as referred to above is controlled by the rate of bromination. But, due to limited solubility of $Br_{10}DPE$ and $Br_9DPE$ in bromine one cannot simply add everything together and then heat the reaction mixture for a period of time. Once precipitated, such materials cannot be redissolved in any reasonable time of 5-10 hours, expecting that then the bromination would be completed. Rather, at any instant of time, the bromine stays saturated in $Br_{10}DPE$. The instant more DPE and/or pb-DPE is added and is brominated to $Br_9DPE$ and $Br_{10}DPE$, something must precipitate due to supersaturation of the bromine with $Br_{10}DPE$. If much $Br_9DPE$ is present when this occurs, it can and will coprecipitate with the $Br_{10}DPE$ inside the particle, leading to low assay product.

Secondly, by slowing down the rate of DPE and/or pb-DPE addition, the rate of precipitation (e.g., lbs/hr) is decreased. Then there is more time for the $Br_9DPE$ to become brominated. Thus, rate of DPE addition (all else being equal) has a very significant affect on the assay of the product, the slower the addition of the DPE and/or pb-DPE, the higher the assay. However, slow DPE and/or pb-DPE addition slows productivity of the plant. To maximize decabromodiphenylethane product production in a commercially-sized plant, the DPE and/or pb-DPE should be added as fast as possible, preferably in, say, about two hours, more or less. To overcome the resulting low assay problem, it has been found necessary to speed up the bromination. Pursuant to this invention, this is done by:

1) adding more aluminum-based catalyst, i.e., operating the process with a higher concentration of aluminum-based catalyst in the reaction mixture; and/or
2) increasing the temperature of the reaction. This of course can require pressure greater than atmospheric pressure but this does not constitute a significant problem in the operation of a commercial plant.

If one elects to make a selection as between approaches 1) and 2), the approach of 2) is deemed preferred due to cost of the catalyst and removal and disposal of the resulting aluminum salts. Nevertheless, approach 1) is commercially-feasible and can be used. Indeed, it is possible, and may be more preferred in commercial operation to utilize a combination of approaches 1) and 2) along with a commercially-feasible DPE and/or pb-DPE feed rate to the reaction mixture comprised of excess bromine in the liquid state and the aluminum-based catalyst.

Accordingly, one example of a coordinated set of conditions pursuant to this invention for producing a decabromodiphenylethane product that comprises at least about 99.0 GC area percent of decabromodiphenylethane ($Br_{10}DPE$), with the balance consisting essentially of nonabromodiphenylethane ($Br_9DPE$), involves use of the following:

1) a minimum feed time of about two hours in a batch bromination;
2) the presence in the reaction mixture of at least about 2000 ppm of aluminum as an aluminum-based Lewis acid bromination catalyst resulting from addition to the reaction mixture containing excess liquid bromine of either metallic aluminum in a form such as aluminum foil, aluminum powder, aluminum turnings, aluminum filings, etc., or an aluminum halide in which the halogen atoms are chlorine and/or bromine, preferably aluminum chloride or aluminum bromide; and
3) a reaction temperature of at least about 60° C. for most, if not all, of the total bromination reaction time.

Another example of a coordinated set of conditions pursuant to this invention for producing a decabromodiphenylethane product that comprises at least about 99.0 GC area percent of decabromodiphenylethane ($Br_{10}DPE$), with the balance consisting essentially of nonabromodiphenylethane ($Br_9DPE$), involves use of the following:

1) a minimum feed time of about six hours in a batch bromination;
2) the presence in the reaction mixture of at least about 700 ppm of aluminum as an aluminum-based Lewis acid bromination catalyst resulting from addition to the reaction mixture containing excess liquid bromine of either metallic aluminum in a form such as aluminum foil, aluminum powder, aluminum turnings, aluminum filings, etc., or an aluminum halide in which the halogen atoms are chlorine and/or bromine, preferably aluminum chloride or aluminum bromide; and
3) a reaction temperature of at least about 60° C. for most, if not all, of the total bromination reaction time On the basis of the foregoing illustrative examples of coordinated reaction conditions those of skill in the art will now be able to develop other sets of properly coordinated sets of reaction conditions which will produce a decabromodiphenylethane product that comprises at least about 99.0 GC area percent of decabromodiphenylethane ($Br_{10}DPE$), with the balance consisting essentially of nonabromodiphenylethane ($Br_9DPE$). Thus, on the basis of a few experimental reactions one of skill in the art can readily determine in any given case a set of conditions for achieving this important and highly desirable result. For example, if a pilot reaction is carried out at 60° C. with a two hour feed time and X ppm of aluminum charged in one of the forms illustrated above in an excess of liquid bromine, and the desired assay is not obtained, on the basis of the foregoing illustrations, one could either increase the temperature or the concentration of aluminum in the system, or both, knowing that doing either would increase the assay.

FURTHER DETAILED DESCRIPTION OF EMBODIMENTS OF THIS INVENTION

As used herein including the claims:
1) The term "reaction-derived" means that the composition of the product is reaction determined and not the result of use of downstream purification techniques, such as recrystallization or chromatography, or like procedures that can affect the chemical composition of the product. Adding water or an aqueous base such as sodium hydroxide to the reaction mixture to inactivate the catalyst, and washing away of non-chemically bound impurities by use of aqueous washes such as with water or dilute aqueous bases are not excluded by the term "reaction-derived". In other words, the products are directly produced in the synthesis process without use of any subsequent procedure to remove or that removes nonabromodiphenyl ethane ($Br_9DPE$) from decabromodiphenylethane ($Br_{10}DPE$).

2) Unless otherwise specified, the term "high assay" means that the reaction-derived decabromodiphenylethane product comprises at least about 99.0 GC area percent of decabromodiphenylethane ($Br_{10}DPE$) with the balance consisting essentially of nonabromodiphenylethane ($Br_9DPE$). Preferred reaction-derived decabromodiphenylethane product comprises at least 99.5% of decabromodiphenylethane and more preferred reaction-derived decabromodiphenylethane product comprises at least 99.7% of $Br_{10}DPE$, in both cases, with the balance consisting essentially of nonabromodiphenylethane ($Br_9DPE$).

3) The term "diphenylethane" means 1,2-diphenylethane unless otherwise specified. 1,2-Diphenylethane is also known as dibenzyl or bibenzyl. The term "partially brominated diphenylethane having a bromine number of less than about two" means that diphenylethane contains an average of less than two bromine atoms as substituents on the phenyl group or groups of the compound.

4) The term "subsurface" denotes that the feed occurs below the surface of the continuous bromine-containing liquid phase of the reaction mixture.

In each process of this invention, the diphenylethane and/or partially brominated diphenylethane with an average bromine number of less than about two is fed to a reaction mixture containing an excess amount of liquid bromine and the appropriate amount of aluminum-based Lewis acid bromination catalyst. The reaction mixture may also contain inert organic solvent or diluent such as such a halogenated hydrocarbon (e.g., bromochloromethane, dibromomethane, 1,2-dibromoethane, 1,2-dichloroethane, 1,1-dibromoethane, tribromomethane, or the like). Such solvent or diluent can be added during the course of the reaction if desired.

The diphenylethane and/or partially brominated diphenylethane can be fed in various forms. For example, it can be fed in admixture with liquid bromine, as a solution in an inert organic solvent or diluent such as referred to above, or as a mixture with both bromine and inert organic solvent or diluent such as referred to above. Alternatively, the diphenylethane and/or partially brominated diphenylethane can be fed in the form of particulate solids or in molten condition.

Excess bromine is used in the Lewis acid catalyzed bromination reaction. Typically, the reaction mixture will contain in the range of at least about 14 moles of bromine per mole of diphenylethane and/or partially brominated diphenylethane to be fed thereto, and preferably, the reaction mixture contains in the range of about 16 to about 25 moles of bromine per mole of diphenylethane and/or partially brominated diphenylethane to be fed thereto. It is possible to use more than 25 moles bromine per mole of diphenylethane but ordinarily this is unnecessary.

The feeds used in the practice of this invention are composed of (i) diphenylethane or (ii) partially brominated diphenylethane having an average bromine number of less than about two, or (iii) both of (i) and (ii). When both diphenylethane and partially brominated diphenylethane are used as feeds, these feed components can be fed as a preformed mixture or they can be fed separately, either concurrently, or sequentially. The components in such mixtures or separate feeds can be in any proportions relative to each other.

Aluminum-based Lewis acid bromination catalysts are used in the practice of this invention. The catalyst component as charged to the reaction mixture can be in the form of metallic aluminum such as in the form of aluminum foil, aluminum turnings, aluminum flakes, aluminum powder, or other subdivided forms of aluminum metal. Alternatively, the catalyst component as charged to the reaction mixture can be in the form of an aluminum halide in which the halogen atoms are chlorine atoms, bromine atoms, or a combination of chlorine atoms and bromine atoms. A feed of aluminum chloride is desirable from the standpoints of economics and ready availability of that material. A feed of aluminum bromide is desirable from the standpoint that it is more soluble in liquid bromine than aluminum chloride and thus can be fed into the reaction zone along with liquid bromine, which is one desirable way to operate. The amount of aluminum-based catalyst used has been referred to above.

The reaction mixture should of course be kept anhydrous and free from exposure to light. The bromination can be conducted on a batch, semi-continuous, or continuous basis. Conduct of the reaction on a batch basis is simpler as it typically enables use of slower feeds and longer reaction times than other modes of operation.

The GC procedure for use in determining the composition of decabromodiphenylethane products whether formed by this invention or otherwise is as follows. The gas chromatography is on a Hewlett-Packard 5890 Series II gas chromatograph equipped with a flame ionization detector, a cool on-column temperature and pressure programmable inlet, and temperature programming capability. The column is a 12QC5 HTS capillary column, 12 meter, 0.15µ film thickness, 0.53 mm diameter, available from SGE, Inc., part number 054657. Conditions were: detector temperature 350° C.; inlet temperature 70° C.; helium carrier gas at 10 mL/min.; inlet pressure 4.0 psig (ca.$1.29 \times 10^5$ Pa), increasing at 0.25 psi/min. to 9.0 psig (ca. $1.63 \times 10^5$ Pa) and holding at 9.0 psig until the end of the run; oven temperature 60° C. with heating at 12° C./min. to 350° C. and holding for 10 min.; and injection mode of cool on-column. Samples were prepared by dissolving, with warming, 0.003 grams in 10 grams of dibromomethane and injection of 2 microliters of this solution. The integration of the peaks was carried out using Target Chromatography Analysis Software from Thru-Put Systems, Inc. However, other and commercially available software suitable for use in integrating the peaks of a chromatograph may be used. Thru-Put Systems, Inc. is currently owned by Thermo Lab Systems, whose address is 5750 Major Blvd., Suite 200, Orlando, Fla. 32819. The address of SGE, Incorporated is 2007 Kramer Lane, Austin, Tex. 78758.

The following examples are presented for purposes of illustration. They are not intended to limit the invention to only the particular operations and conditions used therein. Example 1 illustrates the benefits of forming a high assay reaction-derived decabromodiphenylethane product pursuant to this invention using a high reaction temperature in the bromination reaction.

EXAMPLE 1

The reaction system used was composed of a 500-mL jacketed pressure reactor (available from Ace Glass) equipped with a thermocouple well with thermocouple, mechanical stirrer, ⅟₃₂-inch (ca. 0.08 cm) I.D. dip tube and a 0° C. cooled condenser, the latter being connected to a Teflon polymer back-pressure regulator by means of ¼-inch (ca. 0.64 cm) O.D. Teflon polymer tubing. Connected to this ¼-inch Teflon polymer tubing, immediately before the back-pressure regulator were a pressure gauge, provisions for adding a small nitrogen purge, and a connection to the vapor space of a pressure bottle. The reactor was heated by circulating heated water, the temperature of which was controlled to give the desired reaction temperature, through the jacket.

The reactor was charged with 2.06 grams aluminum chloride and 920 grams bromine. The pressure bottle was charged with 116 grams of 40 wt % diphenylethane (DPE) in dibromomethane. The bromine was sparged with HBr gas for 10 minutes then allowed to stand for 2 hours. The mixture was heated to 82.7° C. under pressure and feed of the DPE solution at a constant rate began at time 0. The following data were recorded.

| Time, min. | Temperature, ° C. | Pressure, psig |
|---|---|---|
| 0 | 82.7 | 27 (2.88 × 10$^5$ Pa) |
| 3 | 84.6 | |
| 6 | 86.9 | 40 (3.77 × 10$^5$ Pa) |
| 10 | 85.5 | 41 (3.84 × 10$^5$ Pa) |
| 13 | 84.6 | 41 (3.84 × 10$^5$ Pa) |
| 22 | 83.6 | 41 (3.84 × 10$^5$ Pa) |
| 36 | 84.2 | 40 (3.77 × 10$^5$ Pa) |
| 40 | 84.2 | 40 (3.77 × 10$^5$ Pa) |
| 49 | 84.5 | 41 (3.84 × 10$^5$ Pa) |
| 58 | 84.7 | 41 (3.84 × 10$^5$ Pa) |
| 71 | 84.3 | |

At time 71 minutes all DPE solution had been fed. The reactor was cooled under pressure to 35° C., vented and 150 mL ice water added. The contents of the reactor were transferred to a 1-liter flask set for distillation, 300 mL water added, and bromine distilled to 100° C. The mixture was cooled to 40° C., 40 grams 25% NaOH added, and the solid collected and washed with water. After oven drying a sample analyzed as about 99.3 area percent decabromodiphenylethane ($Br_{10}DPE$).

The following example is presented as a comparative example not of this invention. This comparative example shows the effect of lower temperature, use of low catalyst concentration, and fast feed of diphenylethane (DPE).

COMPARATIVE EXAMPLE

The equipment used in this example was a 500-mL jacketed pressure reactor (available from Ace Glass) equipped as described in Example 1. The reactor was charged with 2.1 grams aluminum chloride and 925 grams bromine. It was pressured to 10 psig (1.70×10$^5$ Pa) with HBr. The pressure bottle was charged with 116 grams of 40% DPE in dibromomethane. The bromine was heated to 61.5° C. and feed of DPE solution began at time 0. The following data were collected.

| Time, min. | Temperature, ° C. | Pressure, psig |
|---|---|---|
| 0 | 61.5 | 31 (3.15 × 10$^5$ Pa) |
| 10 | 63.7 | 34 (3.36 × 10$^5$ Pa) |
| 15 | 60.3 | 31 (3.15 × 10$^5$ Pa) |
| 30 | 60.6 | 31 (3.15 × 10$^5$ Pa) |
| 45 | 61.0 | 36 (3.50 × 10$^5$ Pa) |
| 62 | 60.8 | 34 (3.36 × 10$^5$ Pa) |
| 75 | 60.9 | 36 (3.50 × 10$^5$ Pa) |
| 86 | 61.2 | 35 (3.43 × 10$^5$ Pa) |

At time 88 minutes all DPE solution had been added. It was stirred 6 minutes longer then the mixture cooled partially and vented. Workup of the reaction mixture in as in Example 1 gave a product that analyzed as 96.8% $Br_{10}DPE$, the balance being $Br_9DPE$.

Examples 2-4 illustrate the production of high assay reaction-derived decabromodiphenylethane product using high concentrations of aluminum-based Lewis acid bromination catalyst. Example 4 also shows that somewhat lower temperatures can be used while still obtaining high assay reaction-derived product.

EXAMPLE 2

The 500-mL jacketed pressure reactor (available from Ace Glass) equipped as described in Example 1 was again used. The reactor was charged with 10.4 grams aluminum chloride and 924 grams dry bromine. This was sparged with anhydrous HBr as it was heated to 50° C. over 10 minutes. The pressure bottle was charged with 40 wt % DPE in dibromomethane. The reactor was heated to 60° C. and a continuous feed of the DPE solution, via the diptube that was subsurface to the bromine, began at time 0 by use of a peristaltic pump. The following data were recorded.

| Time, min. | Temperature, ° C. | Pressure, psig |
|---|---|---|
| 0 | 60 | 8 (1.57 × 10$^5$ Pa) |
| 21 | 60.5 | 14 (1.98 × 10$^5$ Pa) |
| 27 | 61.2 | 22 (2.53 × 10$^5$ Pa) |
| 35 | 61.4 | 27 (2.88 × 10$^5$ Pa) |
| 55 | 61.5 | 34 (3.36 × 10$^5$ Pa) |
| 80 | 61.2 | 41 (3.84 × 10$^5$ Pa) |
| 105 | 62.1 | 40 (3.77 × 10$^5$ Pa) |
| 135 | 61.9 | 42 (3.91 × 10$^5$ Pa) |
| 165 | 61.9 | 42 (3.91 × 10$^5$ Pa) |
| 203 | 61.9 | 39 (3.70 × 10$^5$ Pa) |
| 240 | 61.8 | 41 (3.84 × 10$^5$ Pa) |
| 280 | 62.0 | 41 (3.84 × 10$^5$ Pa) |
| 327 | 62.0 | 41 (3.84 × 10$^5$ Pa) |
| 401 | 62.2 | 41 (3.84 × 10$^5$ Pa) |
| 435 | 62.2 | 43 (3.98 × 10$^5$ Pa) |
| 460 | 62.2 | 41 (3.84 × 10$^5$ Pa) |

At time 477 minutes the DPE feed was discontinued at which time 95 grams of solution had been fed. The reactor was cooled partially, vented, and 150 mL ice water added. The contents of the reactor were transferred to a 1-liter reactor set for distillation. An additional 300 mL water was added and bromine distilled to 100° C. After cooling to 55° C. the solid was collected, water washed, and oven dried at 125° C. GC analysis indicated the reaction-derived decabromodiphenylethane product contained 99.8% of $Br_{10}DPE$.

EXAMPLE 3

A 1-liter Morton flask was equipped with a heating mantle, thermocouple, mechanical stirrer, two 0° C. condensers in series and a ¼-inch (ca. 0.64 cm) O.D. diptube with a ¹⁄₁₆-inch (ca. 0.16 cm) I.D. orifice at the end for feeding DPE solution mixed with bromine. Bromine condensate was collected by means of a Dean-Stark trap between the water-cooled condenser and the reactor and used to dilute the DPE solution in the diptube. The two feeds to the diptube were fed by means of peristaltic pumps. The DPE solution was fed down an ⅛" (ca. 0.32 cm) O.D. tube that extended to near the bottom of the ¼-inch diptube and the bromine was fed into the annular space, such that the two mixed in the diptube immediately prior to exiting from the orifice. The reactor was charged with 10.0 grams of $AlCl_3$ and 1039 grams of bromine. A graduated cylinder was charge with 82 ml (125 grams) of a 40% solution of DPE in dibromomethane. The reactor was brought to reflux and feeding of bromine and DPE solution commenced at the same time. The DPE solution was fed at a rate of about 0.7 mL per minute. Bromine was pumped at 15-21 mL per minute. The following data were collected.

| Time, min. | Temperature, ° C. |
|---|---|
| 0 | 58.9 |
| 4 | 58.6 |
| 20 | 59.0 |
| 47 | 59.4 |
| 66 | 59.8 |
| 88 | 60.6 |
| 102 | 61.2 |
| 110 | 61.7 |
| 113 | 62.0 |

The mixture was refluxed 5 min. longer, cooled to 35° C., and 450 mL water added. The reactor was set for distillation and bromine distilled to 100° C. The mixture was cooled to 40° C. and the solid collected and washed well with water then oven dried. GC analysis showed 99.8% $Br_{10}DPE$, the balance being $Br_9DPE$.

EXAMPLE 4

A 1-liter Morton flask equipped with thermocouple well and thermocouple, mechanical stirrer, a $\frac{1}{32}$" (ca. 0.08 cm) I.D. diptube, and 0° C. cooled Friedrichs condenser was charged with 10 grams aluminum chloride and 982 grams bromine. A graduated cylinder was changed with 82 ml (125 grams) of a 40% solution of DPE in dibromomethane. The DPE solution was fed via the diptube by use of a peristaltic pump. The following data were collected.

| Time, min. | Temperature, ° C. |
|---|---|
| 0 | 59.3 |
| 10 | 64.2 |
| 30 | 54.6 |
| 50 | 55.1 |
| 65 | 55.5 |
| 80 | 56.0 |
| 102 | 57.0 |
| 110 | 57.2 |
| 116 | 57.6 |

At time 116 minutes all DPE solution had been fed. The feed line was rinsed by adding 2 mL dibromomethane. The mixture was heated to reflux of 63° C. over 4 minutes then cooled, 450 ml water added and bromine distilled to 100° C. It was cooled and the solid collected and washed well with water. Analysis of a sample showed 99.16% $Br_{10}DPE$, the balance being $Br_9DPE$.

It will be noted that in Examples 2, 3, and 4, the amounts of aluminum chloride catalyst used were equivalent to 2276, 1947, and 2060 parts per million of aluminum per million parts of bromine.

To further assist in understanding the concept of coordination of the reaction variables as specified herein, the term "coordinate" or "coordinated" is intended to denote that proper order or relation among the specified reaction variables is to be effected or has been effected so that the variables act in combination to achieve the specified objective(s). Another way of looking at these terms is that they call for suitable correlation of the variables whereby the specified objective is, or the specified objectives are, achieved through mutual or reciprocal relation or orderly connection among the variables.

The high assay reaction-derived decabromodiphenylethane products formed in the processes of this invention (hereinafter Product of this invention) may be used as flame retardants in formulations with virtually any flammable material. The material may be macromolecular, for example, a cellulosic material or a polymer. Illustrative polymers are: olefin polymers, cross-linked and otherwise, for example homopolymers of ethylene, propylene, and butylene; copolymers of two or more of such alkene monomers and copolymers of one or more of such alkene monomers and other copolymerizable monomers, for example, ethylene/propylene copolymers, ethylene/ethyl acrylate copolymers and ethylene/propylene copolymers, ethylene/acrylate copolymers and ethylene/vinyl acetate copolymers; polymers of olefinically unsaturated monomers, for example, polystyrene, e.g. high impact polystyrene, and styrene copolymers, polyurethanes; polyamides; polyimides; polycarbonates; polyethers; acrylic resins; polyesters, especially poly(ethyleneterephthalate) and poly(butyleneterephthalate); polyvinyl chloride; thermosets, for example, epoxy resins; elastomers, for example, butadiene/styrene copolymers and butadiene/acrylonitrile copolymers; terpolymers of acrylonitrile, butadiene and styrene; natural rubber; butyl rubber and polysiloxanes. The polymer may be, where appropriate, cross-linked by chemical means or by irradiation. The product of this invention can also be used in textile applications, such as in latex-based back coatings.

The amount of Product of this invention used in a formulation will be that quantity needed to obtain the flame retardancy sought. In general, the formulation and resultant product may contain from about 1 to about 30 wt %, preferably from about 5 to about 25 wt % of Product of this invention. Master batches of polymer containing Product of this invention, which are blended with additional amounts of substrate polymer, typically contain even higher concentrations of Product of this invention, e.g., up to 50 wt % or more.

It is advantageous to use the Product of this invention in combination with antimony-based synergists, e.g., $Sb_2O_3$. Such use is conventionally practiced in all decabromodiphenylethane applications. Generally, the Product of this invention will be used with the antimony based synergists in a weight ratio ranging from about 1:1 to 7:1, and preferably of from about 2:1 to about 4:1.

Any of several conventional additives used in thermoplastic formulations may be used, in their respective conventional amounts, with Product of this invention, e.g., plasticizers, antioxidants, fillers, pigments, UV stabilizers, etc.

Thermoplastic articles formed from formulations containing a thermoplastic polymer and Product of this invention can be produced conventionally, e.g., by injection molding, extrusion molding, compression molding, and the like. Blow molding may also be appropriate in certain cases.

Components referred to by chemical name or formula anywhere in the specification or claims hereof, whether referred to in the singular or plural, are identified as they exist prior to coming into contact with another substance referred to by chemical name or chemical type (e.g., another component, a solvent, or etc.). It matters not what chemical changes, transformations and/or reactions, if any, take place in the resulting mixture or solution as such changes, transformations, and/or reactions are the natural result of bringing the specified components together under the conditions called for pursuant to this disclosure. Thus the components are identified as ingredients to be brought together in connection with performing a desired operation or in forming a desired composition. Also, even though the claims hereinafter may refer to substances, components and/or ingredients in the present tense ("comprises", "is", etc.), the reference is to the substance, component or ingredient as it existed at the time just before it was first contacted, blended or mixed with one or more other substances, components and/or ingredients in accordance with the present disclosure. The fact that a substance, component or ingredient may have lost its original identity through a chemical reaction or transformation during the course of contacting, blending or mixing operations, if conducted in accordance with this disclosure and with ordinary skill of a chemist, is thus of no practical concern.

Except as may be expressly otherwise indicated, the article "a" or "an" if and as used herein is not intended to limit, and should not be construed as limiting, a claim to a single element to which the article refers. Rather, the article "a" or "an" if and as used herein is intended to cover one or more such elements, unless the text expressly indicates otherwise.

Each and every patent or publication referred to in any portion of this specification is incorporated in toto into this disclosure by reference, as if fully set forth herein.

This invention is susceptible to considerable variation in its practice. Therefore the foregoing description is not intended to limit, and should not be construed as limiting, the invention to the particular exemplifications presented hereinabove.

That which is claimed is:

1. A process for preparing high assay reaction-derived decabromodiphenylethane product, which process comprises feeding (i) diphenylethane, (ii) partially brominated diphenylethane having a bromine number less than two, or (iii) both of (i) and (ii) subsurface into the liquid phase of a reaction mixture formed from components comprising excess liquid bromine and aluminum-based Lewis acid bromination catalyst, wherein the temperature of the reaction mixture, the catalyst concentration in the excess bromine in the reaction mixture, and the feed time are coordinated to produce high assay reaction-derived decabromodiphenylethane product, wherein the amount of aluminum in the reaction mixture as the aluminum-based Lewis acid bromination catalyst is equivalent to at least about 2000 parts per million of aluminum per million parts of bromine.

2. A process as in claim 1 wherein the process is conducted on a batch basis with an addition time of in the range of about two to about four hours and at a temperature of at least about 60° C. with the reactants under sufficient pressure to maintain at least bromine in the liquid state.

3. A process as in claim 1 wherein the process is conducted on a batch basis with an addition time of in the range of about four to about six hours and at a temperature of at least about 60° C. with the reactants under sufficient pressure to maintain at least bromine in the liquid state.

4. A process as in claim 1 wherein the process is conducted (i) on a batch basis with an addition time of in the range of about two to about four hours; (ii) at a temperature of at least about 60° C. with the reactants under sufficient pressure to maintain at least bromine in the liquid state; and (iii) with an amount of aluminum-based Lewis acid bromination catalyst in the reaction mixture equivalent to at least about 2000 ppm of aluminum.

5. A process as in claim 1 wherein the process is conducted (i) on a batch basis with an addition time of at least about six hours; (ii) at a temperature of at least about 60° C. with the reactants under sufficient pressure to maintain at least bromine in the liquid state; and (iii) with an amount of aluminum-based Lewis acid bromination catalyst in the reaction mixture equivalent to at least about 700 ppm of aluminum.

6. A process as in claim 1 wherein said aluminum-based Lewis acid bromination catalyst as charged in forming said reaction mixture is aluminum bromide.

7. A process as in claim 1 wherein said aluminum-based Lewis acid bromination catalyst as charged in forming said reaction mixture is aluminum chloride.

8. Reaction-derived decabromodiphenylethane product produced by the process of any of claims 1-7, said product comprising at least about 99.5 GC area percent of decabromodiphenylethane with the balance of the assay consisting essentially of nonabromodiphenylethane.

9. Reaction-derived decabromodiphenylethane product produced by the process of any of claims 1-7, said product comprising at least about 99.7 GC area percent of decabromodiphenylethane with the balance of the assay consisting essentially of nonabromodiphenylethane.

* * * * *